United States Patent
Prendergast (10) Patent No.: US 10,500,241 B2
(45) Date of Patent: Dec. 10, 2019

(54) **COMPOSITIONS COMPRISING *SIRAITIA GROSVENORI* EXTRACTS AND METHODS FOR THE TREATMENT OF INFECTION**

(71) Applicant: Cascade Estates Limited, Quatre Bornes (MU)

(72) Inventor: Patrick T. Prendergast, Byrock (AU)

(73) Assignee: Cascade Estates Limited, Quatre Bornes (MU)

( * ) Notice: Subject to any disclaimer, the term of this patent is extended or adjusted under 35 U.S.C. 154(b) by 0 days.

(21) Appl. No.: 15/819,344

(22) Filed: Nov. 21, 2017

(65) Prior Publication Data

US 2018/0318370 A1 Nov. 8, 2018

Related U.S. Application Data

(63) Continuation of application No. 14/633,320, filed on Feb. 27, 2015, now abandoned, which is a continuation of application No. 12/679,402, filed as application No. PCT/EP2008/062645 on Sep. 22, 2008, now abandoned.

(60) Provisional application No. 60/994,824, filed on Sep. 21, 2007.

(30) Foreign Application Priority Data

Sep. 21, 2007 (GB) .................................. 0718446.8
Nov. 12, 2007 (CN) .......................... 2007 1 0188155

(51) Int. Cl.
| | |
|---|---|
| A61K 36/00 | (2006.01) |
| A61K 36/42 | (2006.01) |
| A61K 31/405 | (2006.01) |
| A61K 31/704 | (2006.01) |
| A61K 45/06 | (2006.01) |

(52) U.S. Cl.
CPC ............ *A61K 36/42* (2013.01); *A61K 31/405* (2013.01); *A61K 31/704* (2013.01); *A61K 45/06* (2013.01)

(58) Field of Classification Search
CPC .................................................... A61K 36/00
See application file for complete search history.

(56) References Cited

U.S. PATENT DOCUMENTS

| | | |
|---|---|---|
| 5,411,755 A | 5/1995 | Downton et al. |
| 2004/0142320 A1 | 7/2004 | Wychowski et al. |
| 2006/0003032 A1 | 1/2006 | Sha |
| 2006/0003053 A1 | 1/2006 | Ekanayake et al. |
| 2007/0116839 A1 | 5/2007 | Prakash et al. |

FOREIGN PATENT DOCUMENTS

| | | | |
|---|---|---|---|
| CN | 1709120 A | * | 12/2005 |
| JP | 2001322934 A | | 11/2001 |

OTHER PUBLICATIONS

Akihisa et al., "Cucurbitane glycosides from the fruits of Siraitia gros venorii and their inhibitory effects on Epstein-Barr virus activation," J Nat Prod, 70(5): 783-788 (2007).
Database WPI Week 200403 Thomson Scientific, London, GB; AN 2004-026731 and JP 2003 277270 A (Univ Nippon) Oct. 2, 2003.
Database WPI Week 200733 Thomson Scientific, London, GB; AN 2007-349386 and JP 2007 106733 A (Saraya KK) Apr. 26, 2007.
Kamei et al., "New pharmacological functions of Luo Han Guo," Database Chemabs Chemical Abstracts Service, Columbus, Ohio, US, Database accession No. 2005 : 320651.
Pinho et al., "GB virus C/hepatitis G virus and other putative hepatitis non A-E viruses," Revista do Institute de Medicina Tropical de Sao Paulo, 38(6): 441-50 (1996).
PureLo provided by the Applicant on Jul. 5, 2012 during prosecution of EP application No. 08804570.3.
Tsang et al., "Isolation and characterization of a new ribosome inactivating protein, momorgrosvin, from seeds of the monk's fruit Momordica grosvenorii," Life Sci, 68(7): 773-784 (2001).
Ukiya et al., "Inhibitory effects of cucurbitane glycosides and other triterpenoids from the fruit of Momordica grosvenori on epstein-barr virus early antigen induced by tumor promoter 12-O-tetradecanoylphorbol-13-acetate," J Agric Food Chem, 50(23): 6710-6715 (2002).
Wachi et al., "A case of acute cholestatic hepatitis associated with fluvastatin sodium," J Med Soc Toho Univ, 48(2): 153-158 (2001).

* cited by examiner

*Primary Examiner* — Qiuwen Mi
(74) *Attorney, Agent, or Firm* — Foley Hoag LLP (57) ABSTRACT

A method for the treatment and/or prophylaxis of a viral infection in a subject is provided wherein the method comprises the steps of providing a therapeutically effective amount of a composition comprising an extract of the fruit of *Siraitia grosvenori* Swingle and administering the composition to the subject. The fruit from which the extract is derived is Luo Han Guo. The extract comprises at least one triterpene glycoside, which may be in the form of a mogroside compound. The extract has been shown to be effective in the treatment of viral infections such as hepatitis C and HIV. Also provided are pharmaceutical compositions comprising at least one triterpene glycoside, or an analogue, metabolite, precursor, derivative, pharmaceutically active salt or pro-drug thereof.

19 Claims, 3 Drawing Sheets

COMPOSITIONS COMPRISING *SIRAITIA GROSVENORI* EXTRACTS AND METHODS FOR THE TREATMENT OF INFECTION

RELATED APPLICATIONS

This application is a continuation application of U.S. application Ser. No. 14/633,320, filed on Feb. 27, 2015; which is a continuation application of U.S. application Ser. No. 12/679,402 filed on Apr. 23, 2010; which is the 371 U.S. national stage of PCT/EP08/062645, filed Sep. 22, 2008, which claims priority to U.S. Provisional Application 60/994,824 filed Sep. 21, 2007; Great Britain Application No. 0718446.8, filed Sep. 21, 2007; and Chinese Application 2007/10188155.2 filed Nov. 12, 2007. The entire contents of each of these applications are hereby incorporated by reference.

FIELD OF THE INVENTION

The present invention relates to methods for the prophylaxis and/or treatment of viral infections, such as hepatitis C and HIV. The invention further relates to compositions for use in the treatment and/or prophylaxis of viral infections.

BACKGROUND TO THE INVENTION

Luo Han Guo (also known as Luo Han Kuo) is a fruit of the *Siraitia grosvenori* Swingle (formerly *Momoridca grosvenori* Swingle) belonging to the Cucurbitaceae species. These fruits are cultivated in parts of China and extract of the Luo Han Guo plant is currently manufactured and marketed as a natural low-calorie sweetener, for example, PURELO™. U.S. Pat. No. 5,411,755 describes a process for preparing a sweet juice from Luo Han Guo fruit. The sweetness of the extract from Luo Han Guo is due to the presence of highly stable triterpene glycosides, known as mogrosides, which are about 250 to 300 times sweeter than sucrose. These compounds possess a triterpene backbone with two to six glucose units attached. Examples of cucurbitane glycosides purified from *Siraitia grosvenori* include 20-hydroxy-11-oxomogroside $IA_1$, 11-oxomogroside IIE, 11-oxomogroside $IA_1$, mogroside IIE, mogroside III, mogroside IV, mogroside V, siamenoside I, triterpenoid glycoside V, neogroside, Kaempferol 7-α-ʟ-rhamnopyranoside, Kaempferol 3,7-α-ʟ-dirhamnopyranoside, 11-oxomogroside III, 11-Dehydroxymogroside III, 11-oxomogroside IV, mogroside II, mogroside VI, 11-oxo-mogroside and siamcroside-I. Mogrosides have been shown to have beneficial effects in the treatment of diabetes, cancer and inflammation.

Statins are compounds that are known to have a lowering effect on levels of LDL-cholesterol in the human blood. Statins inhibit hydroxymethylglutaryl coenzyme A (HMG-CoA) reductase, the rate-determining enzymatic step in cholesterol biosynthesis. Currently available statins include lovastatin, simvastatin, pravastatin, fluvastatin (LESCOL®, CANEF®), cerivastatin and atorvastatin. Fluvastatin (disclosed in U.S. Pat. No. 4,739,073) is administered as a sodium salt and is an entirely synthetic compound that is in part structurally distinct from the fungal derivatives of this class, which contain a hexahydronaphthalene ring.

Hepatitis C (HCV), formerly referred to as blood-borne non-A, non-B hepatitis virus (NANBV), is a transmissible disease which was first identified in individuals who had received blood transfusions. Chronic hepatitis C virus is an insidious and slow-progressing disease having a significant negative impact on the quality of life. It can eventually result in cirrhosis of the liver, decompensated liver disease and/or hepatocellular carcinoma.

Alpha interferon mono-therapy is commonly used to treat infection with chronic hepatitis C. However, this treatment is not always effective and sometimes results in intolerable side effects depending on the dosage and the duration of therapy.

The general anti-viral therapeutic Ribavirin has been proposed as a mono-therapy treatment for chronic hepatitis C infection. However, this mono-therapy treatment has been found to be relatively ineffective and, furthermore, presents its own undesirable side effects.

An alternative therapeutic approach combining alpha interferon and Ribavirin has also been proposed. Preliminary results suggest that such a combination therapy may be more effective then either alpha interferon or Ribavirin mono-therapy. However, the combined use of alpha interferon and Ribavirin does not eradicate HCV-RNA in a long-term, effective manner.

There is therefore a need to provide a therapy which has efficacy in the treatment of chronic hepatitis C infection. Desirably, such a therapeutic composition or treatment regimen will eradicate HCV-RNA in a long-term, effective manner.

Furthermore, in addition to the treatment of subjects infected with HCV, there is a pressing need to provide means of treating HCV-contaminated blood or blood products. Post-transfusion hepatitis (PTH) occurs in approximately 10% of transfused patients, with HCV accounting for up to 90% of these cases. The disease frequently progresses to chronic liver damage in 25 to 55% of cases.

Acquired immune deficiency syndrome (AIDS) is a disease characterized by failure of the immune system. It is attributable to a virus called human immunodeficiency virus (HIV), which is a member of the retrovirus family of lipid envelope viruses, which is very prevalent in the animal kingdom. HIV infects and takes over certain cells of the immune system, using these cells to replicate. This causes the infected cells to function improperly and die prematurely, thus weakening the immune system. HIV infection results in disturbances of the entire immune defense mechanism. In particular, T4 or helper cells are prevented from carrying out their role in the regulation of the immune response. This HIV-induced T4 reduction results in the development of frequent and eventually fatal opportunistic infections caused by pathogenic organisms such as viruses, bacteria, protozoa or fungi.

Anti-viral agents that inhibit replication of viruses have been known since the mid 1980's. The overall goal of anti-HIV therapy is to slow or stop the replication process, and thereby slow or stop the progression of HIV disease and the destruction of the immune system. Many drugs are now available for inhibiting the replication of the HIV virus. However, their side effects are often so severe that treatment must be halted allowing HIV resistant strains to quickly develop. Current anti-HIV therapies can be categorized into groups based on which step in the virus's life cycle they target or how they do it. Examples of anti-HIV therapies include nucleoside analogue reverse-transcriptase inhibitors, non-nucleoside analogue reverse-transcriptase inhibitors and protease inhibitors. The first two groups work by mimicking one of the building blocks of DNA and thus interfering with reverse transcription, a process essential for HIV replication. The third group, protease inhibitors, works at a later stage in the viral life cycle after the virus has successfully infected the cell and is attempting to replicate.

These drugs ultimately slow down the replication of viral DNA. However, they do not rid the body of the virus but merely act to slow down and reduce the severity of the development of the infection.

The number of patients infected with HIV has significantly increased in recent years. There is therefore a need for the development of a more efficacious and less toxic treatment for HIV.

Many of the anti-viral therapies which are currently available are directed towards targeting viral components and are therefore prone to compensatory viral evasion mechanisms. Treatments aimed at interfering with, or preventing, viral replication, either by enhancing antiviral responses or by inhibiting proviral activities within the host cell have greater potential for controlling the virus without selective pressure on the virus itself to mutate in a compensatory manner.

SUMMARY OF THE INVENTION

According to a first aspect of the present invention, there is provided a method for the treatment and/or prophylaxis of a viral infection in a subject, the method comprising the steps of:
providing a therapeutically affective amount of a composition comprising at least one triterpene glycoside or an analogue, metabolite, precursor, derivative, pharmaceutically active salt or pro-drug thereof; and
administering the composition to the subject.

According to a second aspect of the invention there is provided at least one triterpene glycoside or an analogue, metabolite, precursor, derivative, pharmaceutically active salt or pro-drug thereof for use in the treatment and/or prophylaxis of a viral infection.

A third aspect of the present invention provides for use of at least one triterpene glycoside or an analogue, metabolite, precursor, derivative, pharmaceutically active salt or pro-drug thereof in the preparation of a medicament for the treatment and/or prevention of a viral infection.

According to a further aspect of the invention, there is provided a composition comprising at least one triterpene glycoside or an analogue, metabolite, precursor, derivative, pharmaceutically active salt or pro-drug thereof.

According to a further aspect of the invention, there is provided a pharmaceutical composition comprising at least one triterpene glycoside or an analogue, metabolite, precursor, derivative, pharmaceutically active salt or pro-drug thereof and at least one pharmaceutically acceptable diluent, carrier or excipient.

According to a further aspect of the invention, there is provided a composition comprising at least one triterpene glycoside or an analogue, metabolite, precursor, derivative, pharmaceutically active salt or pro-drug thereof for use as a medicament.

According to a further aspect of the present invention, there is provided a method for the treatment and/or prophylaxis of a viral infection in a subject, the method comprising the steps of:
providing a therapeutically effective amount of a composition comprising an extract of the fruit of *Siraitia grosvenori* Swingle; and
administering the composition to the subject.

According to a further aspect of the invention there is provided an extract of the fruit of *Siraitia grosvenori* Swingle for use in the treatment and/or prophylaxis of a viral infection.

A further aspect of the present invention provides for use of an extract of the fruit of *Siraitia grosvenori* Swingle in the preparation of a medicament for the treatment and/or prevention of a viral infection.

According to a further aspect of the invention, there is provided a composition comprising an extract of the fruit of *Siraitia grosvenori* Swingle.

According to a further aspect of the invention, there is provided a pharmaceutical composition comprising an extract of the fruit of *Siraitia grosvenori* Swingle and at least one pharmaceutically acceptable diluent, carrier or excipient.

According to a further aspect of the invention, there is provided a composition comprising an extract of the fruit of *Siraitia grosvenori* Swingle for use as a medicament.

DESCRIPTION OF THE FIGURES

The present invention will now be described with reference to the following examples which are provided for the purpose of illustration and are not intended to be construed as being limiting on the present invention, and further with reference to the figures as described briefly below.

DETAILED DESCRIPTION OF THE INVENTION

The present invention is directed to the use of at least one triterpene glycoside and/or an extract of the fruit of *Siraitia grosvenori* Swingle as an antiviral.

In certain embodiments, the at least one triterpene glycoside or extract is derived from the Cucurbitaceae plant, in particular from the fruit of the Cucurbitaceae plant. In certain embodiments, the plant is of the variety *Siraitia grosvenori* Swingle and typically the fruit is a fruit of *Siraitia grosvenori* Swingle. In certain embodiments, the fruit is Luo Han Guo, also known as Luo Han Kuo.

In certain embodiments, the extract is an extract of Luo Han Guo. In certain embodiments, the extract is derived from the Luo Han Guo fruit using the process described in U.S. Pat. No. 5,411,755, the entire contents of which are herein incorporated by reference.

In certain embodiments, the invention relates to use of an extract of a Cucurbitaceae plant in the preparation of a medicament for the treatment and/or prevention of a viral infection.

In certain embodiments, the extract comprises at least one triterpene glycoside.

In certain embodiments, the at least one triterpene glycoside is a mogroside or an analogue, metabolite, precursor, derivative, pharmaceutically active salt or pro-drug thereof. Typically the mogroside is derived from a plant of the Cucurbitaceae species, in particular the fruit of the Cucurbitaceae species. In certain embodiments, the plant is *Siraitia grosvenori* Swingle (formerly *Momoridca grosvenori* Swingle). Typically the fruit is Luo Han Guo.

In certain embodiments, the at least one triterpene glycoside is selected from the group consisting of, but not limited to, 20-hydroxy-11-oxomogroside $IA_1$, 11-oxomogroside IIE, 11-oxomogroside $IA_1$, mogroside IIE, mogroside III, mogroside IV, mogroside V, siamenoside I, triterpenoid glycoside V, neogroside, Kaempferol 7-α-ʟ-rhamnopyranoside, Kaempferol 3,7-α-ʟ-dirhamnopyranoside, 11-oxomogroside III, 11-Dehydroxymogroside III, 11-oxomogroside IV, mogroside II, mogroside VI, 11-oxo-mogroside and siamcroside-I, and analogues, metabolites, precursors, derivatives, pharmaceutically active salts or pro-drugs thereof.

In certain embodiments, the at least one triterpene glycoside is mogroside V or an analogue, metabolite, precursor, derivative, pharmaceutically active salt or pro-drug thereof.

In certain embodiments, the at least one triterpene glycoside is 20-hydroxy-11-oxomogroside $IA_1$ or an analogue, metabolite, precursor, derivative, pharmaceutically active salt or pro-drug thereof.

In certain embodiments, the at least one triterpene glycoside is 20-hydroxy-11-oxomogroside $IA_1$ or an analogue, metabolite, precursor, derivative, pharmaceutically active salt or pro-drug thereof.

In certain embodiments, the at least one triterpene glycoside is 11-oxomogroside IIE or an analogue, metabolite, precursor, derivative, pharmaceutically active salt or pro-drug thereof.

In certain embodiments, at least one triterpene glycoside is 11-oxomogroside $IA_1$ or an analogue, metabolite, precursor, derivative, pharmaceutically active salt or pro-drug thereof.

In certain embodiments, the at least one triterpene glycoside is mogroside IIE or an analogue, metabolite, precursor, derivative, pharmaceutically active salt or pro-drug thereof.

In certain embodiments, the at least one triterpene glycoside is mogroside III or an analogue, metabolite, precursor, derivative, pharmaceutically active salt or pro-drug thereof.

In certain embodiments, the at least one triterpene glycoside is mogroside IV or an analogue, metabolite, precursor, derivative, pharmaceutically active salt or pro-drug thereof.

In certain embodiments, the at least one triterpene glycoside is siamenoside I or an analogue, metabolite, precursor, derivative, pharmaceutically active salt or pro-drug thereof.

In certain embodiments, the at least one triterpene glycoside is neogroside or an analogue, metabolite, precursor, derivative, pharmaceutically active salt or pro-drug thereof.

In certain embodiments, the at least one triterpene glycoside is triterpenoid glycoside V or an analogue, metabolite, precursor, derivative, pharmaceutically active salt or pro-drug thereof.

In certain embodiments, the at least one triterpene glycoside is Kaempferol 7-α-ʟ-rhamnopyranoside or an analogue, metabolite, precursor, derivative, pharmaceutically active salt or pro-drug thereof.

In certain embodiments, the at least one triterpene glycoside is Kaempferol 3,7-α-ʟ-dirhamnopyranoside or an analogue, metabolite, precursor, derivative, pharmaceutically active salt or pro-drug thereof.

In certain embodiments, the at least one triterpene glycoside is 11-oxomogroside III or an analogue, metabolite, precursor, derivative, pharmaceutically active salt or pro-drug thereof.

In certain embodiments, the at least one triterpene glycoside is 11-Dehydroxymognoside III or an analogue, metabolite, precursor, derivative, pharmaceutically active salt or pro-drug thereof.

In certain embodiments, the at least one triterpene glycoside is 11-oxomogroside IV or an analogue, metabolite, precursor, derivative, pharmaceutically active salt or pro-drug thereof.

In certain embodiments, the at least one triterpene glycoside is mogroside II or an analogue, metabolite, precursor, derivative, pharmaceutically active salt or pro-drug thereof.

In certain embodiments, the at least one triterpene glycoside is mogroside VI or an analogue, metabolite, precursor, derivative, pharmaceutically active salt or pro-drug thereof.

In certain embodiments, the at least one triterpene glycoside is 11-oxo-mogroside or an analogue, metabolite, precursor, derivative, pharmaceutically active salt or pro-drug thereof.

In certain embodiments, the at least one triterpene glycoside is siamcroside-I or an analogue, metabolite, precursor, derivative, pharmaceutically active salt or pro-drug thereof.

In certain embodiments, the composition or extract comprises a mixture of triterpene glycosides, for example mogrosides such as mogroside IV or mogroside V. Typically, mogroside V is the major constituent of the mixture. In certain embodiments, the composition or extract comprises more than 50% mogrosides, typically more than 70% and preferably more than 80%.

In certain embodiments, the composition or extract comprises at least one mogroside in an isolated form wherein the at least one mogroside has been isolated and purified from Luo Han Guo. In certain embodiments, the composition or extract comprises the at least one mogroside in the form of a crude extract of Luo Han Guo. In certain embodiments, the at least one mogroside or extract is provided in the form of a natural sweetener or juice, for example, using the process described in U.S. Pat. No. 5,411,755. In certain embodiments, the juice is dried and the extract provided in a powder form. In certain embodiments, the at least one mogroside or extract comprises a bacterially-transformed mogroside. In certain embodiments, the at least one mogroside or extract comprises a mogroside in a synthetic form.

In certain embodiments, the mogroside is selected from the group of compounds having the chemical formula shown in formula 1 below:

Formula 1

| | $R_1$ | $R_2$ | $R_3$ | $R_4$ |
|---|---|---|---|---|
| 20-hydroxy-11-oxomogroside I $A_1$ (1) | —H | —Glc | =O | —OH |
| 11-oxomogroside II E (2) | —Glc | —Glc | =O | —H |
| 11-oxomogroside I $A_1$ (3) | —H | —Glc | =O | —H |
| mogroside II E (4) | —Glc | —Glc | ⋯OH, H | —H |
| mogroside III (5) | —Glc | —Glc—⁶Glc | ⋯OH, H | —H |
| mogroside IV (6) | —Glc—⁶Glc | —Glc—⁶Glc | ⋯OH, H | —H |
| mogroside V (7) | —Glc—⁶Glc | —Glc—⁶Glc (²Glc) | ⋯OH, H | —H |

In certain embodiments, the at least one triterpene glycoside is an analogue, metabolite, precursor, derivative, pharmaceutically active salt or pro-drug of one of the compounds shown in formula 1.

Without wishing to be bound by theory, it is hypothesized that a composition comprising an extract of the Luo Han Guo fruit, such as at least one triterpene glycoside or an analogue, metabolite, precursor, derivative, pharmaceutically active salt or pro-drug thereof, inhibits or suppresses replication of a viral infection by interfering with the replicative or other essential functions of the viral infection or the host cell. Specifically, it is postulated that triterpene glycoside interacts with the cytoplasmic environment of the host cell but does not directly interface with the viral infection. This is advantageous as the risk of the virus developing resistance to the treatment is reduced. Accordingly, an effective anti-viral therapy is provided having minimal risk of conferring resistance to the virus.

In certain embodiments, the at least one triterpene glycoside, or an analogue, metabolite, precursor, derivative, pharmaceutically active salt or pro-drug thereof, is halogenated or is administered in combination with a halogen salt or with a halogenated salt. In further embodiments, the halogen or halogenated salt may be administered before or after the composition has been administered. Without wishing to be bound by theory, the inventor predicts that the production and/or activity of neutrophils and/or monocytes is enhanced when a halogen salt or a halogenated salt is administered along with the triterpene glycoside of when the triterpene glycoside is halogenated.

The invention further relates to a combined medicament comprising a statin and the at least one triterpene glycoside or an analogue, metabolite, precursor, derivative, pharmaceutically active salt or pro-drug thereof. The components of the combined medicament work in a synergistic manner such that the dose of each therapeutic compound required in order to achieve a therapeutic and/or prophylactic effect is reduced when both components are administered to an individual. Specifically, statins such as fluvastatin may be used to extend the lower range of the effectiveness of triterpene glycosides such as mogroside V or mogroside IV such that lower doses of the triterpene glycoside may be used. The invention further relates to a combined medicament comprising a statin and the extract.

Accordingly, in certain embodiments, the method aspects of the present invention further comprise the step of:
administering a therapeutically effective amount of a secondary composition comprising a statin or an analogue, metabolite, derivative, pharmaceutically active salt, precursor or prodrug thereof.

In certain embodiments, the statin is selected from the group consisting of mevastatin, lovastatin, pravastatin, simvastatin, cerivastatin, fluindostatin, velbstatin, fluvastatin, dalvastatin, dihydrocompactin, compactin, atorvastatin, bervastatin and NK-104, ZD-4522.

In certain embodiments, the statin is fluvastatin.

In certain embodiments, the statin composition may be administered to the subject simultaneously with the triterpene glycoside or extract composition.

In certain embodiments, the statin composition is administered separately to the triterpene glycoside or extract composition.

In certain embodiments, the statin composition may be administered to the subject sequentially with the triterpene glycoside or extract composition. Where the compounds are administered sequentially, in certain embodiments the statin composition is administered prior to the triterpene glycoside or extract composition. In certain further embodiments, the triterpene glycoside or extract composition is administered prior to the statin composition.

In certain embodiments, the statin composition and the triterpene glycoside or extract composition are co-administered. Co-administration means that these components may be administered together as a composition or as part of the same unitary dose or the same therapeutic regimen. Where the compositions are administered separately, the "co-administration" of the compositions does not impose a restriction on the timing, frequency, dosage or order of when the compounds can be administered.

In certain embodiments, the statin and triterpene glycoside or extract compositions are provided by different routes of administration. Further, said compositions may be in the same or different forms, for example a solid and a liquid.

In certain embodiments, the statin composition and the triterpene glycoside or extract are provided in a combined medicament, for example as a single composition.

In certain embodiments, the statin composition comprises fluvastatin as a sodium salt.

The chemical IUPAC name for fluvastatin is 7-[3-(4-fluorophenyl)-1-(1-methylethyl)-1H-indol-2-yl]-3,5-dihydroxy-hept-6-enoic acid.

In one embodiment, fluvastatin is defined by chemical formula 2 as shown below.

The inventor has also identified that the therapeutic compositions of the present invention comprising at least one triterpene glycoside or an analogue, metabolite, precursor, derivative, pharmaceutically active salt or pro-drug thereof, or an extract of the Luo Han Guo fruit have utility when administered to a subject along with a further antiviral compound. Such a combination therapy would, in particular, have utility in relation to viral infections having a high pathogenicity and, furthermore, would be effective at reducing the development of viral drug resistance.

Accordingly, in certain embodiments, the methods of the present invention include the step of:
administering a therapeutically effective amount of a further antiviral compound.

In certain embodiments, said further anti-viral compound is administered in addition to said secondary composition, which comprises statin or a related compound.

In certain embodiments, the further antiviral compound may be administered to the subject simultaneously with the triterpene glycoside or extract composition.

In certain embodiments the further antiviral compound is provided separately to the triterpene glycoside or extract composition.

In certain embodiments, the further antiviral compound may be administered to the subject sequentially with the triterpene glycoside or extract composition. Where the compounds are administered sequentially, in certain embodiments the further antiviral compound is administered prior to the triterpene glycoside or extract composition. In certain further embodiments, the triterpene glycoside or extract composition is administered prior to the further antiviral compound.

In certain embodiments, the further antiviral compound and the triterpene glycoside or extract composition are co-administered.

In certain embodiments, the further antiviral compound and the triterpene glycoside or extract composition are provided by different routes of administration. Further, said further antiviral compound and composition may be in the same or different forms, for example a solid and a liquid.

In certain embodiments, the further antiviral compound and the triterpene glycoside or extract composition are provided in a combined medicament, for example as a single composition.

The antiviral compound may be selected from the group consisting of nucleoside analogues (AZT; ddC; ddI; d4T; 3TC, BW 1592; PMEA/bis-POM PMEA; dOTC; DAPD); non-nucleoside reverse transcriptase inhibitors (delavirdine; DMP 266; HBY097; loviride; nevirapine, emivirine; AG1549; PNU 142721; Calanolide A; DPC961); protease inhibitors (ABT-378; ritonavir; nelfinavir; BW 141; KNI-272; indinavir; saquinavir; L-756,423; DMP-450; BMS-232630); ALX40-4C; hydroxyurea; lobucavir; pentafuside; T-1249; PRO 542; FP-21399; AMD 3100; HE-2000; peptide T; Abacavir; Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Coviracil; Cytarabine Hydrochloride; Delavirdine Mesylate; Desciclovir; Didanosine; Disoxaril; Edoxudine; Emivirine; Emtricitabine; Enviradene; Enviroxime; Epivir; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Indinavir; Kethoxal; Lamivudine; Lobucavir; Lodenosine; Lopinavir, Memotine Hydrochloride; Methisazone; Nelfinavir; Nevirapine; Penciclovir; Pirodavir; Ribavirin; Rimantadine Hydrochloride; Saquinavir Mesylate; Ritonavir; Somantadine Hydrochloride; Sorivudine; Statolon; Stavudine; Tenofovir; Tilorone Hydrochloride; Trifluridine; Valacyclovir Hydrochloride; Vidarabine; Vidarabine Phosphate; Vidarabine Sodium Phosphate; Tipranavir, Viroxime; Zalcitabine; Zidovudine; Zinviroxime and Interferons alpha, beta and gamma.

In certain embodiments wherein the virus is HIV, the further antiviral compound is a drug commonly used in HAART (highly active antiretroviral therapy). It has been shown that HIV can quickly mutate to avoid the effect of one drug alone and that it is therefore advantageous to use drugs effective against HIV in a combination "cocktail" to fight the virus.

Some of the compounds (e.g. the at least one triterpene glycoside, statin and further antiviral compound) for use in the methods of the present invention may exist as stereoisomers and/or geometric isomers, e.g. they may possess one or more asymmetric and/or geometric centres and so may exist in two or more stereoisomeric and/or geometric forms. The present invention contemplates the use of all of the individual stereoisomers and geometric isomers of those compounds and mixtures thereof. The terms used in the claims encompass these forms, provided said forms retain the appropriate functional activity (though not necessarily to the same degree).

The present invention also includes the use of solvate forms of these compounds in the methods of the present invention. The terms used in the claims encompass these forms, provided said forms retain the appropriate functional activity (though not necessarily to the same degree).

The present invention also includes the use of pro-drug forms of these compounds in the methods of the present invention. The terms used in the claims encompass these forms. Examples of pro-drugs include entities that have certain protected group(s) and which may not possess pharmacological activity as such, but may, in certain instances, be administered (such as orally or parenterally) and thereafter metabolised in the body to form pharmacologically active compounds.

As defined herein, the term "metabolite" means any substance which results from, or is produced by, the metabolism or digestion by a subject of a compound administered to said subject. In pharmaceutical terms, the phrase relates to the product which remains after digestion or metabolism, particularly by the liver, has occurred.

In certain embodiments of the present invention, the compounds for use in the methods and compositions of the present invention, such as triterpene glycoside and/or statin, may be a mimetic. As used herein, the term "mimetic" relates to any compound, which includes, but is not limited to, a peptide, polypeptide, antibody or other organic chemical, which has the same qualitative activity or effect as the triterpene glycoside or statin compounds of the invention. The terms used in the claims encompass mimetics, provided said mimetics retain the appropriate functional activity (though not necessarily to the same degree).

In certain embodiments of the present invention, the compounds for use in the methods and compositions of the present invention may be a derivative of a triterpene glycoside compound or a statin. The term "derivative" as used herein includes chemical modification of the triterpene glycoside compound and/or statin, said derivatives retaining the desired chemical activity of the compounds.

In certain embodiments of the present invention, the compounds for use in the methods and compositions of the present invention may be an analogue of a triterpene glycoside compound or statin. The term "analogue" as used herein is intended to refer to compounds having the same functional activity, though not necessarily to the same degree.

In certain embodiments of the present invention, the triterpene glycoside compound may be chemically modified, for example by halogenation. The chemical modification of the compound may either enhance or reduce hydrogen bonding interaction, charge interaction, hydrophobic interaction, van der Waals interaction or dipole interaction between the compound and the target.

As herein defined, the expression "pharmaceutically acceptable salts" extends to both pharmaceutically acceptable acid addition salts and pharmaceutically acceptable cationic salts. A "pharmaceutically acceptable cationic salt" includes, but is not limited to, cationic salts such as the alkali metal salts, for example, sodium or potassium, as well as alkaline earth metal salts, for example magnesium, ammonium salts and the like. A "pharmaceutically acceptable acid addition salts" includes, but is not limited to salts such as hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Pharmaceutically-acceptable salts are well known to those skilled in the art, and for example include those mentioned by Berge et al, in J. Pharm. Sci. 66, 1-19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

The compounds for use in the methods of the present invention may be prepared by chemical synthesis techniques. It will be apparent to those skilled in the art that sensitive functional groups may need to be protected and deprotected during synthesis of a compound of the invention. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be epimerised, for example if a base is used in a reaction with a substrate having an optical centre comprising a base-sensitive group. It should be possible to circumvent potential problems such as this by choice of reaction sequence, conditions, reagents, protection/deprotection regimes and the like as these are well known in the art.

When reference is made herein to a "triterpene glycoside" such as mogroside, this term is intended to embrace the triterpene glycoside in its free base form in addition to pharmaceutically acceptable salts of such triterpene glycosides. Furthermore, said triterpene glycoside may extend to an enantiomer or diasterioisomers of said triterpene glycoside compound, wherein the desired functional activity of said triterpene glycoside compound is maintained in that form.

The triterpene glycoside compounds or related salts for use in the invention may be separated and purified by conventional methods.

In certain embodiments, the statin provided in the statin composition is at least one statin compound or a stain-like compound. The terms "statin compound" and "statin-like compound" embrace analogues, metabolites, derivatives, pharmaceutically active salts, such as hydroxy acid salts, precursors, pro-drugs, enantiomers, and stereoisomers of statins or statin-like compounds.

In certain embodiments, the statin salt is a hydroxy acid salt. In certain embodiments, said hydroxy acid salt is a metabolite of a statin pro-drug which is administered to, and metabolised by, the subject in need of treatment.

In certain embodiments, the statin metabolite results from the metabolism of a compound following administration to a subject.

In certain embodiments, the statin pro-drug is a composition which, following administration to a subject, is metabolised into a molecular or structural form which is active in terms of providing the effects desired by a statin compound.

In certain embodiments, the composition is a combined medicament comprising at least one statin compound, pro-drug or metabolite thereof along with triterpene glycoside or a derivative, analogue or metabolite thereof.

In certain further embodiments, the statin compound or statin-like compound may be an optical or geometric isomer, a nontoxic pharmacologically acceptable acid addition salt, an N-oxide, an ester, a quaternary ammonium salt, or a prodrug of any of the above-listed statin compounds.

In certain embodiments, amorphous forms of the statins may be administered to a subject.

In certain embodiments, the pharmaceutically acceptable diluent, excipient or carrier may be chosen based on the intended route of administration of the resulting pharmaceutical composition. In certain embodiments, the composition is formulated in beta-hydroxycyclodextrin. In certain embodiments, the pharmaceutically acceptable carrier is selected from the group consisting of cyclodextrin, alpha-cyclodextrin, beta-cyclodextrin, (beta-hydroxypropylcyclodextrin) gamma-cyclodextrin and vitamin E oil.

In certain embodiments, the composition is formulated in an enteric coating made of a polymer. Typically, the enteric coating comprises a polymer or copolymer selected from the group consisting of poly (lactic-glycolic acid) polyester, cellulose acetate phthalate, hydroxypropyl-methyl cellulose phthalate poly (butyl methacrylate), (2-dimethyl aminoethyl) methacrylate and methyl methacrylate.

The terms "a combined preparation" or "combined medicament" or "combined composition" as used herein define a "kit of parts" in the sense that two or more of the combination partners, i.e. (a) the triterpene glycoside or extract composition, (b) the statin composition and (c) the further anti-viral compound, as defined above, can be dosed independently or by use of different fixed combinations with distinguished amounts of the combination partners (a), (b) and (c), i.e., simultaneously or at different time points. The parts of the kit of parts can then be administered simultaneously or administered sequentially or separately, for example chronologically staggered at different time points, and with equal or different time intervals for any part of the kit of parts.

Typically the time intervals of the administration of the dosage forms are chosen such that the effect on the treated disease resulting from the combined use of the parts is larger than the effect which would be obtained by use of only any one of the combination partners (a), (b) and (c).

The ratio of the total amounts of the combination partners to be administered in the combined preparation can be varied, for example, in order to cope with the needs of a subject to be treated.

Typically the amount of the statin composition and the triterpene glycoside or extract composition is selected such that a synergism results from the administration of the compositions, synergism being an effect which is more than an additive effect resulting from the combination of the statin composition and the triterpene or extract composition. Further advantages may be the reduction in side effects or reduction in effective dosage of one or both compositions.

In various further aspects, the present invention extends to a pharmaceutical pack comprising one or more compartments wherein at least one compartment comprises one or more of the compounds as defined herein, or a composition or combined medicament as defined herein or a medicament as defined herein.

In certain embodiments, the viral infection is by a virus of the Flaviviridae family, such as a pestivirus, a flavivirus or a hepacivirus.

In certain embodiments, the viral infection is by a flavivirus. In certain embodiments, the flavivirus is hepatitis C. The compositions and methods of the invention further have utility in preventing or inhibiting the onset and development of infection or other conditions associated with hepatitis C, such as cirrhosis of the liver, decompensated liver disease, chronic liver damage and/or hepatocellular carcinoma. The compositions and methods of the invention further have utility in the treatment of hepatitis contaminated blood products, in particular blood products contaminated with hepatitis C.

In certain embodiments, the viral infection is by a retrovirus. In certain embodiments, the retrovirus is HIV, such as HIV1 or HIV2. In certain embodiments, the retrovirus is HIV1.

In certain embodiments, the viral infection may be by any one of the viruses selected from the group consisting of, but not limited to, influenza virus, hepatitis A, hepatitis B, hepatitis C, hepatitis D, hepatitis E, hepatitis F, hepatitis G, hepatitis H, autoimmune hepatitis and Respiratory Syncytical Virus (RSV). The influenza virus may be a type A influenza virus or a type B influenza virus. In certain embodiments, the virus is a hepatitis-causing virus selected from the group consisting of, but not limited to, the Epstein-Barr virus (EBV), cytomegalo virus (CMV), yellow fever, Bovine Viral Diarrhoea Virus (BVDV), hog cholera virus and sheep border disease virus.

In certain embodiments, the viral infection is by any one of the viruses selected from one or more flavivirus or togavirus infections including, but not limited to, California encephalitis virus, St. Louis encephalitis virus, western equine encephalitis virus, eastern equine encephalitis virus, Colorado tick fever virus, LaCrosse encephalitis virus, Japanese encephalitis virus, yellow fever virus, Venezuelan equine encephalitis virus, Murray valley fever virus, tick-borne encephalitis viruses, GB virus A, GB virus B, GB virus C, Dengue virus 1, Dengue virus 2, Dengue virus 3, Dengue virus 4, Semliki Forest virus and Sindbis virus.

In certain further embodiments, the viral infection may be derived from a rubivirus, such as human rubella virus, pestiviruses, such as mucosal disease viruses, for example, bovine virus diarrhoea virus, hog cholera virus and sheep border disease virus, reteroviruses, such as a human immunodeficiency virus, for example HIV1 or HIV2, simian immunodeficiency viruses, a recombinant human simian immunodeficiency virus, a feline immunodeficiency virus, a feline or murine leukaemia virus, a feline or murine sarcoma virus, Rote viral infections in children and Marburg viruses.

In certain embodiments, the viral infection results in an AIDS related syndrome.

In certain embodiments, viral replication is inhibited or suppressed.

In certain embodiments, the viral infection is a retroviral infection and the method of the present invention encompasses treatment and/or prophylaxis of complications or consequences of retroviral infection.

In certain embodiments, the viral infection is caused by a lipid envelope virus.

As used herein, the term "subject" refers to an animal, preferably a mammal and in particular a human. A "subject" in the context of the present invention therefore includes and encompasses mammals, such as humans, primates and livestock animals (e.g. sheep, pigs, cattle, horses, donkeys); laboratory test animals, such as mice, rabbits, rats and guinea pigs; and companion animals, such as dogs and cats. It is preferred for the purposes of the present invention that the mammal is a human. The term "subject" is interchangeable with the term "patient" as used herein.

In certain embodiments, the subject may be an immunosuppressed animal or human. In certain embodiments, the subject is an immunocompromised AIDS patient or is infected with a retrovirus such as the HIV virus showing the AIDS related complex (ARC).

In certain embodiments, the subject is a neonate. Administration may be carried out prior to delivery of the neonate and/or during delivery of the neonate.

The triterpene glycoside or extract composition may be administered to a subject via any suitable route. Typically, a delivery system is selected which will enhance solubility and provide maximal bioavailability.

In certain embodiments wherein the viral infection to be treated is hepatitis, the composition containing the extract or the at least one triterpene glycoside, such as mogroside, may be formulated and designed so that upon administration, it has maximum bioavailability to the liver and hepatitis-infected cells of the body.

In certain embodiments, the extract or the triterpene glycoside, such as mogroside, is delivered to virally infected cells by incorporating the extract or the triterpene glycoside composition into a liposome or carbohydrate vehicle. The liposome or carbohydrate vehicle can be specifically targeted to infected viral cells by placing antibodies directed to viral antigens on the surface of the liposome or vehicle. This is advantageous in that it allows the liposome or carbohydrate vehicle to selectively target virus-infected cells. In certain embodiments, liposomes are provided carrying high concentrations of at least one mogroside to infected cells.

In certain embodiments, routes of administration may include, but are not limited to, parenterally (including subcutaneous, intramuscular and intravenous, by means of, for example a drip patch), oral, rectal (suppositories), nasal, gastric, topical (including buccal and sublingual), infusion, vaginal, intradermal, intraperitoneally, intracranially, intrathecal and epidural administration. In certain embodiments, the composition is administered via oral or nasal inhalation. For administration via the oral or nasal inhalation routes, typically the active ingredient will be in a suitable pharmaceutical formulation and may be delivered using a mechanical form including, but not restricted to an inhaler, nebuliser device or a nasal spray. Further, where the oral or nasal inhalation route is used, administration by a SPAG (small particulate aerosol generator) may be used.

In certain embodiments, the route of administration is oral or parenteral, for example, intravenously (that is by injection, infusion or continuous drip), intramuscularly or rectally by suppository.

For intravenous injection, the active ingredient will be in the form of a parenterally acceptable aqueous solution which is pyrogen-free and has suitable pH, isotonicity and stability. Methods of preparing suitable solutions using, for example, isotonic vehicles such as sodium chloride injection, Ringer's injection, dextrose solution and Lactated Ringer's injection will be known to persons skilled in the art. Appropriate non-aqueous carriers may also be used and examples include cyclodextrin, preferably hydroxypropyl beta cyclodextrin, mixed oils (vitamin E oil), polyethylene glycol and ethyl oleate. A preferred carrier is cyclodextrin in water. Preservatives, stabilisers, buffers, antioxidants and/or other additives may be included as required to enhance isotonicity and chemical stability.

Pharmaceutical compositions for oral administration may be in tablet, solid, capsule, powder or liquid form. A tablet may comprise a solid carrier such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solutions or glycols such as ethylene glycol, propylene glycol or polyethylene glycol may be included. Suitable formulations for oral administration further include hard or soft gelatin capsules, dragees, pills, tablets, including soft-coated tablets, troches, lozenges, melts, powders, micronized particles, non-micronized particles, solutions, emulsions, elixirs, suspensions, syrups or inhalations and controlled release forms thereof.

Further forms of oral administration include addition of the composition to animal feed and/or drinking water for administration to animals in the treatment and/or prophylaxis of viral infection in animals.

In certain embodiments, administration is topical. Suitable formulations for topical administration include creams, gels, jellies, mucilages, pastes and ointments. The compounds may be formulated for transdermal administration, for example in the form of transdermal patches so as to achieve systemic administration.

The triterpene glycoside or extract composition may also be administered via microspheres, liposomes, other microparticulate delivery systems or sustained release formulations placed in certain tissues including blood.

In certain embodiments, the triterpene glycoside or extract composition may be implanted into a subject or injected using a drug delivery system.

In certain embodiments, the triterpene glycoside or extract composition may be administered in the form of an infusion solution or as a nasal inhalation or spray.

The pharmaceutical composition according to the present invention may be administered locally or systemically. Systemic administration is understood to refer to any mode or route of administration that results in effective amounts of active triterpene glycoside or extract appearing in the blood or at a site remote from the site of administration.

In certain embodiments, the pharmaceutical composition according to the present invention may be administered intermittently. This allows the subject to suspend therapy for periods without the worry of inactivity of the drug resulting from the development of a viral resistant strain.

In certain embodiments, the extract or triterpene glycoside, such as mogroside, is micnonized. The term "micronized" is intended to mean that the compound has been micronized in accordance with any process for micronizing, a number of which are known in the art. The micronized particles preferably include a percentage of particles having a diameter of about 10 microns, or less, preferably 5 microns or less. For example, in a certain aspect of the invention, at least 80% of the particles in a formulation of micronized particles have a diameter of less than 5 microns. An alternative to micronizing a compound is to solubilize the compound and put it into liposomes of appropriate size. The manufacture of liposomes and the insertion of active ingredients into such liposomes are well known in the art.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7th Edition ISBN 0-633305-72-7, the entire disclosures of which is herein incorporated by reference.

The triterpene glycoside or extract is preferably administered to a subject in a "therapeutically effective amount", this being an amount sufficient to show benefit to the subject. In particular, the benefit may be the treatment, partial treatment or amelioration of at least one symptom associated with the viral infection, or the prevention or partial inhibition of the onset of at least one symptom associated with the viral infection. The severity and/or time of onset of the at least one symptom may be reduced. Where the context demands, a "therapeutically effective amount" is an amount which induces, promotes, stimulates or enhances the development of an antiviral response by the subject.

The actual amount administered, and the rate and time-course of administration, will depend on the nature and severity of the viral infection to be treated. Prescription of treatment, e.g. decisions on dosage etc., is ultimately within the responsibility and at the discretion of general practitioners and other medical doctors, and typically takes account of the viral infection to be treated, the condition of the individual patient, the site of delivery, the method of administration and other factors known to practitioners. The precise dose will depend upon a number of factors, including the precise nature of the form of the triterpene glycoside compound to be administered.

Preferably, a dose is administered such as to produce a circulating concentration of the triterpene glycoside and/or its metabolites sufficient to reduce viral loads as monitored by, e.g., viral titer methods or by PCR.

In certain embodiments, the composition is in the form of a unit dose that comprises 5-500 mgs of one or more mogrosides.

In certain embodiments, the composition is administered at a concentration of 6 µg/ml. This concentration has been shown to be particularly effective in the treatment of HIV.

In certain embodiments, the composition is administered at a concentration of greater than 40 µg/mL, more preferably greater than 100 µg/mL. This concentration has been shown to be particularly effective in the treatment of BVDV.

In certain embodiments, the composition is administered daily to a subject.

In certain embodiments, the composition may be used in ex vivo applications to kill viruses. The virus may be any of the viruses listed above. For example, the composition may be used for disinfecting equipment, walls and floors. The composition may also be used in the disinfection of blood products, in particular, blood products contaminated with viruses such as hepatitis C.

As used herein, the term "treatment" and associated terms such as "treat" and "treating" mean the prevention or reduction of the viral infection or the prevention or reduction of the progression, severity and/or duration of any symptom associated with the viral infection, wherein said reduction results from the administration of a composition of the invention. The term "treatment" refers to any regimen that can benefit a subject. The treatment may be in respect of an existing condition or may be a prophylactic (preventative) treatment. Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Accordingly, therapeutic and prophylactic treatment includes amelioration of the symptoms of a particular condition or preventing or otherwise reducing the risk of developing a particular condition. The term "prophylactic" may be considered as including reducing the severity or the onset of a particular condition.

Unless otherwise defined, all technical and scientific terms used herein have the meaning commonly understood by a person who is skilled in the art in the field of the present invention.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

EXAMPLES

Example 1

Anti-Viral Activity of Luo Han Guo Extract Against Bovine Viral Diarrhoea Virus

Materials and Methods

An extract of Luo Han Guo was obtained using the process described in U.S. Pat. No. 5,411,755 and tested for antiviral activity against Bovine Viral Diarrhoea Virus (BVDV), strain NADL. BVDV is a flavivirus in the same family as the human hepatitis C virus. Hepatitis C cannot be grown in tissue culture so BVDV is used as a model virus due to the structural similarities between these two viruses.

The Luo Han Guo extract can be stored at room temperature and is water soluble. The Luo Han Guo extract was tested independently at a wide range of concentrations. The extract was tested in two assays, one at 100, 50, 25, 12.5 and 6.25 µg/mL and the other at 3600, 1200, 400, 133.3 and 44.4 µg/mL.

*Bos taurus* (BT) turbinate cells were used as host cells for the virus. After the cells were plated and allowed to grow overnight, The extract was added and then the virus was inoculated into the cultures. The cultures were allowed to grow for 7 days and then a fluorometric cytoproliferation assay was run. The data from all replicate cultures was averaged and compared to the growth of the negative controls (no virus or extract). The extract was present during absorption and in the media for the duration of the assays. A titration was run on the virus under the assay conditions but without the extract to determine the optimal viral inoculum for the antiviral assay. A dilution of $10^{-4}$ of the stock virus was determined to be the correct inoculum for the antiviral assays. The growth medium used was Dulbecco's Minimum Eagle's Medium and 10% filtered horse serum.

Cultures with virus and no extract were used as positive controls. Cultures of uninfected cells only provided negative controls. Cytotoxicity controls were provided using the extract at all concentrations used, but without viral inoculum.

Results

Tables 1 and 2 show the cytotoxicity and antiviral percentage of negative control and the inhibition index for various concentrations of the extract.

Figure 1:
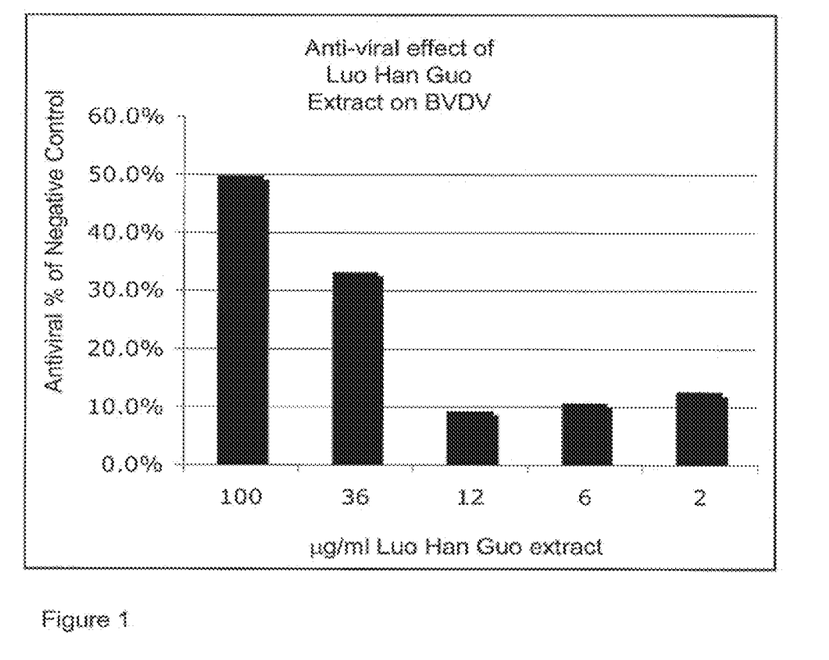
FIG. 1 shows the anti-viral activity of an extract of Luo Han Guo fruit against Bovine Viral Diarrhoea Virus (BVDV)

The results for ranges 2 to 100 µg/ml of extract for the antiviral percentage of negative control shown in Table 2 are graphed in FIG. 1.

The inhibition index was calculated as one minus the ratio of the average fluorescent units of the positive control to the average fluorescent units of infected cultures with a particular concentration of extract (1−(average positive control÷average with extract)). 0 represents no inhibition. 0.9 to 1 represents the best inhibition. The inhibition index helps define the dosages at which a drug is most effective.

In this type of cytoproliferation assay, the outcome is a race between the virus and the experimental compound. If the virus is slow to exhibit killing of the cell, the experimental compounds can do a more thorough job, but if the virus is very aggressive, like BVDV, and kills quickly, the experimental compounds cannot catch up. The percent of the negative control does not take into account how aggressive the virus is. It merely compares the growth of the cells, in particular cultures, to the growth of the negative control.

The inhibition index on the other hand is based on the positive control. It is an index of how much better the cells grow with the compound as compared to the positive control (infected cells without compound) where the closer the value is to 1, the better the action.

TABLE 1

Percent of negative control and inhibition index for high and low range concentrations of Luo Han Guo extract

| Sample | Cytotoxicity (No Virus) % of Neg. Control | Antiviral % of Neg. Control | Inhibition Index | Efficacy |
|---|---|---|---|---|
| Luo Han Guo extract - low range | | | | |
| Negative control | 100% | NA | NA | NA |
| Positive control | NA | 8.5% | NA | NA |
| 100 μg/mL | 83.7% | 4.1% | 0 | None |
| 50 μg/mL | 101.4% | 15.6% | 0.46 | Partial |
| 25 μg/mL | 103.1% | 1.5% | 0 | None |
| 12.5 μg/mL | 114.3% | 2.8% | 0 | None |
| 6.25 μg/mL | 139.3% | 4.6% | 0 | None |
| Luo Han Guo extract - high range | | | | |
| Negative control | 100% | NA | NA | NA |
| Positive control | NA | 0.8% | NA | NA |
| 3600 μg/mL | 86.9% | 28.6% | 0.97 | Partial |
| 1200 μg/mL | 111.5% | 18.6% | 0.96 | Partial |
| 400 μg/mL | 88.8% | 22.6% | 0.96 | Partial |
| 133.3 μg/mL | 114.2% | 10.4% | 0.92 | Partial |
| 44.4 μg/mL | 99.3% | 6.0% | 0.86 | None |

TABLE 2

Percent of negative control and inhibition index for Luo Han Guo extract
Luo Han Guo extract

| Sample | Cytotoxicity (No Virus) % of Neg. Control | Antiviral % of Neg. Control | Inhibition Index | Efficacy |
|---|---|---|---|---|
| Negative control (no drug, no virus) 0 μg/mL | 100% | NA | NA | NA |
| Positive control (no drug, with virus) 0 μg/mL | NA | 8.2% | NA | NA |
| 100 μg/mL | 135.9% | 49.8% | 0.84 | Partial |
| 36 μg/mL | 120.9% | 33.2% | 0.75 | Partial |
| 12 μg/mL | 135.6% | 9.3% | 0.12 | No |
| 6 μg/mL | 123.0% | 10.7% | 0.23 | No |
| 2 μg/mL | 123.1% | 12.6% | 0.35 | No |

The Luo Han Guo extract showed no cytotoxicity over the entire range and was most effective against BVDV at concentrations of greater than 100 μg/mL. At concentrations of less than 100 μg/mL, its effectiveness fell and it had little efficacy at concentrations of 25 μg/mL or less. As noted above, the closer the value of the inhibition index is to 1, the better the action. The high ranges of the extract had values close to 1 (0.86 to 0.97).

The extract was shown not to be able to completely inhibit BVDV but it had an effective range (40 to 3600 μg/mL) where it was able to partially inhibit BVDV proliferation. Although it was unable to completely inhibit BVDV under the conditions of this study, in the inventor's experience no drug has ever completely inhibited BVDV in this cell model nor has any drug in this in vitro system ever been shown to act in any way superior to the extract BVDV, which is the most accurate model for hepatitis C available, is a particularly aggressive virus. Therefore, percentages of the negative control in the range of 50% for BVDV are considered an excellent result. Optimum results were obtained for concentrations of 100 μg/mL where 49.8% negative control was observed.

Example 2

Anti-Viral Activity of the Triterpene Glycoside Mogroside V Against HIV-1

Materials and Methods

Mogroside V was tested for efficacy against HIV-1 strain IIIB using H9 cells as the viral host.

Mogroside V can be stored at room temperature in powder form and is water-soluble. Aqueous stock solution was stored at 4° C. Final reagent dilutions were made in growth media from the aqueous stock solution. Five dilutions of Mogroside V were used: 100, 36, 12, 6 and 2 μg/mL.

H9 cells were used as host cells for the virus. H9 is a human T cell clone selected for high yield permissive growth of HIV-1, cloned from Hut 78, a human T cell lymphoma cell line with an inducer/helper phenotype derived from the peripheral blood of a patient with Sezary Syndrome.

The virus used was HIV-1, Strain IIIB, Catalog No 10-124-000, Lot No. 6M0008-DP, HIV-1 IIIB infects H9 cells but does not consistently cause cytopathic effect (CPE) and therefore viral growth is measured by HIV-1 p24 antigen capture ELISA.

A titration was run on the virus under the assay conditions without the experimental compounds to determine the viral inoculum for the antiviral assay, that is the lowest multiplicity of infection (MOI) that will infect all positive control cultures. The inoculum was approximately seven times the $TCID_{50}$/mL of the stock virus.

Cultures with virus and no Mogroside V provided a positive control. Cultures of uninfected cells only (no Mogroside V) provided a negative control.

Cytotoxicity controls were provided using Mogroside V at all concentrations used, but without viral inoculum. Cytotoxicity was judged from the microscopic inspection of the cells. If the cells with Mogroside V grew more slowly than the negative control, had an altered morphology or appeared necrotic, Mogroside V was judged to be cytotoxic. If the cytotoxicity controls had the same appearance as the negative controls, Mogroside V was considered non-toxic at the concentration in question.

Assay Parameters 1 mL cultures were plated with approximately $2.5 \times 10^5$ cells per culture. Four replicates were run for each assay condition.

The virus was absorbed onto the host cells in the presence of a reduced volume of culture medium for 2 hours. The inoculum was then washed off the cells with phosphate buffered saline. Cultures were then fed with appropriate medium containing Mogroside V to their final volume. The growth medium used was RPMI 1640 with 10% fetal bovine serum and 50 μg/mL gentamicin. Mogroside V was left in the growth medium for the duration of the experiment.

The assay was run for 7 days and re-fed media with appropriate compound concentrations at 4 days.

The amount of virus proliferation was measured using an HIV-1 p24 antigen capture ELISA. At 7 days, supernatants were harvested and frozen. Supernatants were thawed and diluted as necessary, and the HIV-1 p24 ELISA assay was run. Excess supernatant was refrozen and held for 3 months. The HIV-1 p24 pg/mL of replicate cultures were averaged and presented as a percentage of the positive control.

Inhibition Index

The inhibition of Mogroside V at each concentration was calculated by comparing the average amount of virus produced by the experimental cultures (with Mogroside V) to the average of the positive controls (virus but no drug). The inhibition index for each Mogroside V concentration was computed as 1−(average HIV-1 p24 with Mogroside÷V average HIV-1 p24 for the positive control). An inhibition index of zero indicated no efficacy. The closer to 1 the inhibition index was, the greater the efficacy.

Mogroside V was judged to be efficacious against the virus if cultures with Mogroside V had an inhibition index of 0.90 or greater, partially efficacious if cultures had an inhibition index between 0.20 and 0.89 and as having no efficacy if cultures had an inhibition index of less than 0.20.

If Mogroside V had a cytotoxic effect on the host cells as determined by the cytotoxicity control, any decrease in viral growth was judged to be an effect of the cytotoxicity and not an antiviral effect.

Results

Positive controls were positive for HIV-1 p24. The negative control appeared as a healthy growing culture by microscopic inspection and had no HIV-1 p24 signal.

Figure 2:
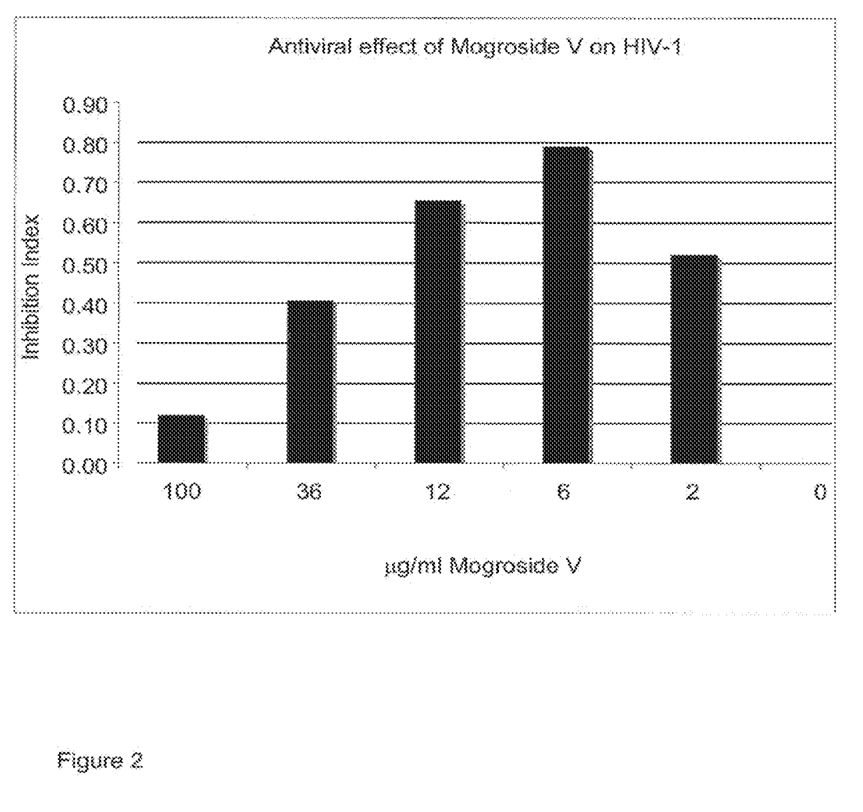
FIG. 2 shows the anti-viral activity of mogroside V against HIV-1 strain IIIB.

Mogroside V was run over a dosage range of 2 to 100 µg/mL and results are provided in Table 3 below. FIG. 2 shows the antiviral effect of these ranges. Mogroside V showed no cytotoxicity, as determined by microscopic inspection, over the entire range of concentrations used and was most effective against HIV-1 at a concentration of 6 µg/mL.

TABLE 3

Cytotoxicity and Inhibition Index for Mogroside V

| Sample (Mogroside V µg/mL) | Cytotoxicity (Appearance of cells) | % Positive Control | Inhibition Index | Efficacy |
|---|---|---|---|---|
| Negative Control | Normal | 0 | NA | NA |
| Positive Control | NA | 100 | 0 | NA |
| 100 µg/mL | Normal | 88 | 0.12 | None |
| 36 µg/mL | Normal | 59 | 0.41 | Partial |
| 12 µg/mL | Normal | 34 | 0.66 | Partial |
| 6 µg/mL | Normal | 21 | 0.79 | Partial |
| 2 µg/mL | Normal | 48 | 0.52 | Partial |

Mogroside V was shown not to be able to completely inhibit HIV-1 under the conditions of this study. However, all concentrations used (with the exception of the highest concentration of 100 µg/ml) were able to significantly suppress viral production. The greatest effect was seen at 6 µg/mL wherein Mogroside V was nearly 80% effective at suppressing HIV-1 replication, with efficacy falling off as the Mogroside V concentration was increased or decreased. Without wishing to be bound by theory, it is hypothesized that the reduction in efficacy at higher concentrations may be due to chemical interactions in solution that inhibit absorption by the cells, for example the formation of inhibiting constructs by Mogroside V.

Example 3

Anti-Viral Activity of Luo Han Guo Extract Against Bovine Viral Diarrhoea Virus (BVDV) When Combined With Flusvastatin Materials and Methods Materials and methods were similar to those outlined in Example 1.

Flusvastatin must be stored between 0° C. and 5° C. and is water soluble. The extract and fluvastatin were tested in combination with two concentrations of the extract, an effective dose (100 µg/mL) and a dose below its effective range for BVDV (6 µg/mL), and five doses of fluvastatin in its effective range (0.313, 0.625, 1.25, 2.5, and 5.0 µg/mL).

Results

Figure 3:
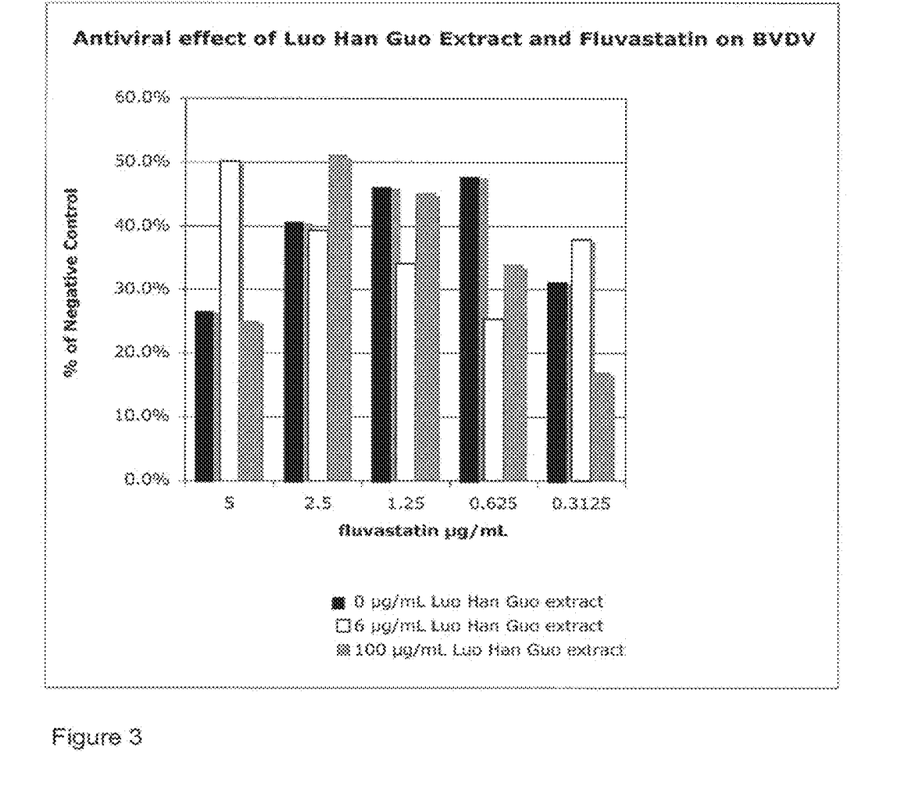
FIG. 3 shows the anti-viral activity of an extract of Luo Han Guo fruit against BVDV when the extract is combined with fluvastatin.

Table 4 shows the percent of negative control and inhibition index for the various concentrations of the extract and fluvastatin. Flusvastatin was shown to extend the lower range of the effectiveness of the extract. In particular, with 6 µg/mL of extract, the inhibition index for 5 and 0.3125 µg/mL fluvastatin was much improved over fluvastatin alone (FIG. 3) or extract alone (FIG. 1).

TABLE 4

Percent of negative control and inhibition index for Luo Han Guo extract and fluvastatin combination.

| Fluvastatin | Cytotoxicity (No Virus) % of Neg. Control | Antiviral % of Neg. Control | Inhibition Index | Efficacy |
|---|---|---|---|---|
| Negative control | 100% | NA | NA | NA |
| Positive control | NA | 8.2% | NA | NA |
| Luo Han Guo Extract (100 µg/mL)/Fluvastatin | | | | |
| 5 µg/mL | 93.6% | 25.2% | 0.67 | Partial |
| 2.5 µg/mL | 113.5% | 51.2% | 0.84 | Partial |
| 1.25 µg/mL | 111.5% | 45.3% | 0.82 | Partial |
| 0.625 µg/mL | 108.4% | 33.9% | 0.76 | Partial |
| 0.3125 µg/mL | 115.0% | 17.0% | 0.52 | No |
| Luo Han Guo Extract (6 µg/mL)/Fluvastatin | | | | |
| 5 µg/mL | 88.7% | 50.3% | 0.84 | Partial |
| 2.5 µg/mL | 103.3% | 39.4% | 0.79 | Partial |
| 1.25 µg/mL | 103.4% | 34.2% | 0.76 | Partial |
| 0.625 µg/mL | 113.8% | 25.5% | 0.68 | Partial |
| 0.3125 µg/mL | 119.4% | 38.0% | 0.78 | Partial |

Fluvastatin Series With 6 µg/mL Luo Han Guo Extract

Luo Han Guo extract at 6 µg/mL in the absence of fluvastatin had no antiviral activity against BVDV (Table 2), but when coupled with fluvastatin at any of the concentrations of fluvastatin used, the combinations all had more antiviral activity than the extract at 6 µg/mL alone (Table 4). At 5 µg/mL, fluvastatin alone had some cytotoxicity and at 0.3125 µg/mL fluvastatin alone had no antiviral activity, but when either of these two concentrations of fluvastatin is combined with the extract at 6 µg/mL, the antiviral effect is greater than that for either fluvastatin or extract alone. With 5 µg/mL fluvastatin and 6 µg/mL extract, the inhibition index was 0.84, and with 0.3125 µg/mL fluvastatin and 6 µg/mL extract, the inhibition index was 0.78 (Table 4), both of which are much improved over fluvastatin alone (data not shown). At the intermediate concentrations of fluvastatin where fluvastatin alone is most efficacious, fluvastatin alone had more antiviral activity than the combination. At 2.5 µg/mL there was not much difference between fluvastatin alone and the combination. The combination with 1.25 µg/mL fluvastatin was about 10% less effective than fluvastatin alone, and at 0.625 µg/mL, the combination was 20% less effective than fluvastatin alone.

Fluvastatin Series With 100 µg/mL Luo Han Guo Extract

Luo Han Guo extract showed good inhibition of BVDV by itself at 100 µg/mL (Table 2). No combination with fluvastatin increased this effectiveness. In fact most combinations with fluvastatin showed less activity than extract alone, except for 2.5 µg/mL fluvastatin where the activity with the extract is the same as if the extract were run alone and the inhibition index was 0.84. Likewise the efficacy of the combination does not improve over that of fluvastatin alone, except for 2.5 µg/mL where there is about a 10% increase in efficacy over fluvastatin alone.

In the ranges where fluvastatin and extract are most effective individually, there was therefore no advantage in combining the two drugs. However, fluvastatin was shown to extend the lower range of the effectiveness of the extract. This would be advantageous where the extract is not tolerated well by a subject or is prohibitively expensive.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A composition comprising a synergistically effective amount of a combination of at least one halogenated triterpene glycoside extracted from the fruit of *Sirailia grosvenori* Swingle and at least one statin for use in the treatment and/or prophylaxis of a viral infection.

2. The composition of claim 1, wherein the at least one halogenated triterpene glycoside or analogue thereof is a mogroside.

3. The composition of claim 1, wherein the viral infection is caused by a virus selected from the group consisting of flavivirus, retrovirus, influenza virus, hepatitis A, hepatitis B, hepatitis D, hepatitis E, hepatitis F, hepatitis G, hepatitis H, autoimmune hepatitis, BVDV and Respiratory Syncytical Virus (RSV).

4. The composition of claim 3, wherein the flavivirus is hepatitis C virus.

5. The composition of claim 3, wherein the retrovirus is HIV.

6. The composition of claim 1, wherein the at least one halogenated triterpene glycoside is selected from the group consisting of neogroside, 20-hydroxy-11-oxomogroside IA$_1$, 11-oxomogroside IIE, 11-oxomogroside IA$_1$, mogroside IIE, mogroside III, mogroside IV, mogroside V, siamenoside I, triterpenoid glycoside V, Kaempferol 7-α-ʟ-rhamnopyranoside, Kaempferol 3,7-α-ʟ-dirhamnopyranoside, 11-oxomogroside III, 11-Dehydroxymogroside III, 11-oxomogroside IV, mogroside II, mogroside VI, 11-oxo-mogroside and siamcroside-I.

7. The composition of claim 1, wherein the extract comprises a halogen salt.

8. The composition of claim 1, wherein the extract includes a secondary antiviral compound.

9. The composition as claimed in claim 1, wherein the statin is selected from the group consisting of mevastatin, lovastatin, pravastatin, simvastatin, cerivastatin, fluindostatin, velbstatin, fluvastatin, dalvastatin, dihydrocompactin, compactin, atorvastatin, bervastatin, NK-104, and ZD-4522.

10. The composition as claimed in claim 9, wherein the statin is fluvastatin.

11. The composition as claimed in claim 10, wherein the fluvastatin comprises a sodium salt.

12. A composition comprising a synergistically effective amount of a combination of at least one halogenated triterpene glycoside extracted from the fruit of *Sirailia grosvenori* Swingle and at least one statin for use in the treatment and/or prophylaxis of hepatitis C.

13. The composition of claim 12, wherein the at least one halogenated triterpene glycoside is a mogroside.

14. The composition of claim 12, wherein the at least one halogenated triterpene glycoside is selected from the group consisting of neogroside, 20-hydroxy-11-oxomogroside IA$_1$, 11-oxomogroside IIE, 11-oxomogroside IA$_1$, mogroside IIE, mogroside III, mogroside IV, mogroside V, siamenoside I, triterpenoid glycoside V, Kaempferol 7-α-ʟ-rhamnopyranoside, Kaempferol 3,7-α-ʟ-dirhamnopyranoside, 11-oxomogroside III, 11-Dehydroxymogroside III, 11-oxomogroside IV, mogroside II, mogroside VI, 11-oxo-mogroside and siamcroside-I.

15. The composition of claim 12, wherein the extract comprises a halogen salt.

16. The composition of claim 12, wherein the extract includes a secondary antiviral compound.

17. The composition as claimed in claim 12, wherein the statin is selected from the group consisting of mevastatin, lovastatin, pravastatin, simvastatin, cerivastatin, fluindostatin, velbstatin, fluvastatin, dalvastatin, dihydrocompactin, compactin, atorvastatin, bervastatin, NK-104, and ZD-4522.

18. The composition as claimed in claim 12, wherein the statin is fluvastatin.

19. The composition as claimed in claim 18, wherein the fluvastatin comprises a sodium salt.

* * * * *